US012558238B2

(12) United States Patent　(10) Patent No.:　US 12,558,238 B2
Oak　(45) Date of Patent:　Feb. 24, 2026

(54) ARTHROPLASTY INSERT

(71) Applicant: Zimmer, Inc., Warsaw, IN (US)

(72) Inventor: Varun Jayant Oak, Singapore (SG)

(73) Assignee: Zimmer, Inc., Warsaw, IN (US)

( * ) Notice: Subject to any disclaimer, the term of this patent is extended or adjusted under 35 U.S.C. 154(b) by 184 days.

(21) Appl. No.: 17/952,703

(22) Filed: Sep. 26, 2022

(65) Prior Publication Data

US 2023/0107257 A1　Apr. 6, 2023

Related U.S. Application Data

(60) Provisional application No. 63/252,851, filed on Oct. 6, 2021.

(51) Int. Cl.
| | |
|---|---|
| *A61F 2/38* | (2006.01) |
| *A61F 2/30* | (2006.01) |
| *A61F 2/48* | (2006.01) |
| *A61F 2/64* | (2006.01) |
| *A61F 2/70* | (2006.01) |
| *A61F 2/74* | (2006.01) |
| *A61F 2/50* | (2006.01) |

(52) U.S. Cl.
CPC .............. *A61F 2/70* (2013.01); *A61F 2/3859* (2013.01); *A61F 2/3872* (2013.01); *A61F 2/389* (2013.01); *A61F 2/484* (2021.08); *A61F 2/64* (2013.01); *A61F 2/748* (2021.08); *A61F 2002/30075* (2013.01); *A61F 2002/30548* (2013.01); *A61F 2002/30586* (2013.01); *A61F 2002/30675* (2013.01); *A61F 2002/30912*

(2013.01); *A61F 2002/30939* (2013.01); *A61F 2002/30943* (2013.01); *A61F 2002/5032* (2013.01); *A61F 2002/704* (2013.01)

(58) Field of Classification Search
CPC ...... A61F 2250/003; A61F 2002/30586; A61F 2002/30939
See application file for complete search history.

(56) References Cited

U.S. PATENT DOCUMENTS

| | | | |
|---|---|---|---|
| RE39,961 E | 12/2007 | Petrofsky et al. | |
| 2002/0143402 A1* | 10/2002 | Steinberg | A61F 2/38 623/23.26 |
| 2005/0197702 A1* | 9/2005 | Coppes | A61F 2/441 623/17.13 |
| 2005/0197814 A1* | 9/2005 | Aram | A61F 2/30942 703/11 |
| 2006/0047341 A1* | 3/2006 | Trieu | A61F 2/442 623/17.12 |

(Continued)

*Primary Examiner* — David H Willse
(74) *Attorney, Agent, or Firm* — Schwegman Lundberg & Woessner, P.A.

(57) ABSTRACT

Systems, methods and apparatuses including an insert having a body with a plurality of bladders therein, a proximal surface and a distal surface. Two or more of the plurality of bladders are in fluid communication with one another. The plurality of bladders are expandable and contractible in volume. The proximal surface shapable by a change in the volume of one or more of the plurality of bladders. The proximal surface is configured to interface with a first arthroplasty implant of the patient. The distal surface is spaced from the proximal surface by the body and is configured to interface with a second arthroplasty implant of the patient.

19 Claims, 12 Drawing Sheets

(56) References Cited

U.S. PATENT DOCUMENTS

| 2007/0276369 | A1* | 11/2007 | Allard | A61F 2/442 |
| | | | | 606/86 A |
| 2010/0262260 | A1 | 10/2010 | Bedard et al. | |
| 2013/0204157 | A1* | 8/2013 | Clark | G01L 1/20 |
| | | | | 73/862.68 |
| 2014/0188229 | A1* | 7/2014 | Hildebrandt | A61L 27/3891 |
| | | | | 623/18.11 |
| 2016/0278944 | A1* | 9/2016 | D'Lima | A61F 2/4657 |
| 2022/0031473 | A1* | 2/2022 | Carter | A61B 34/10 |

* cited by examiner

Processor and Memory 168,172

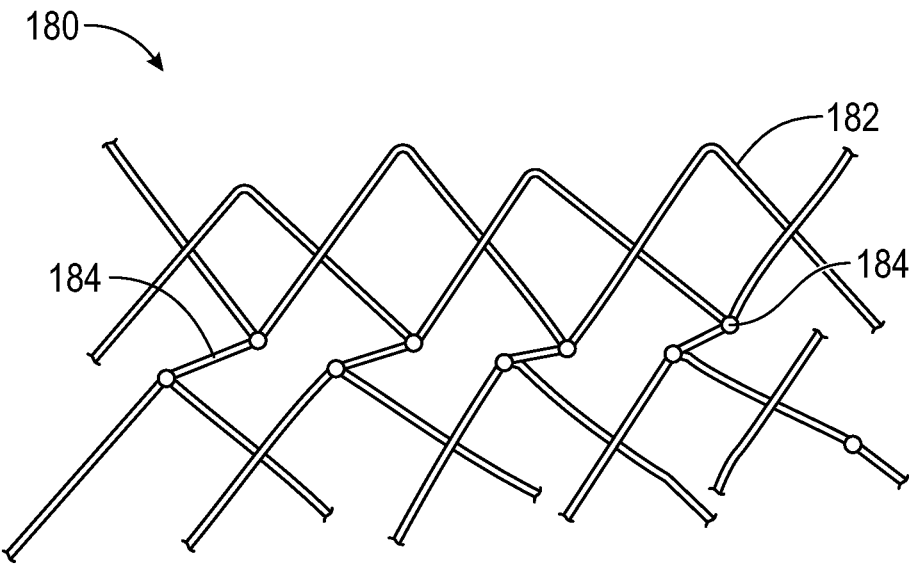
FIG. 9
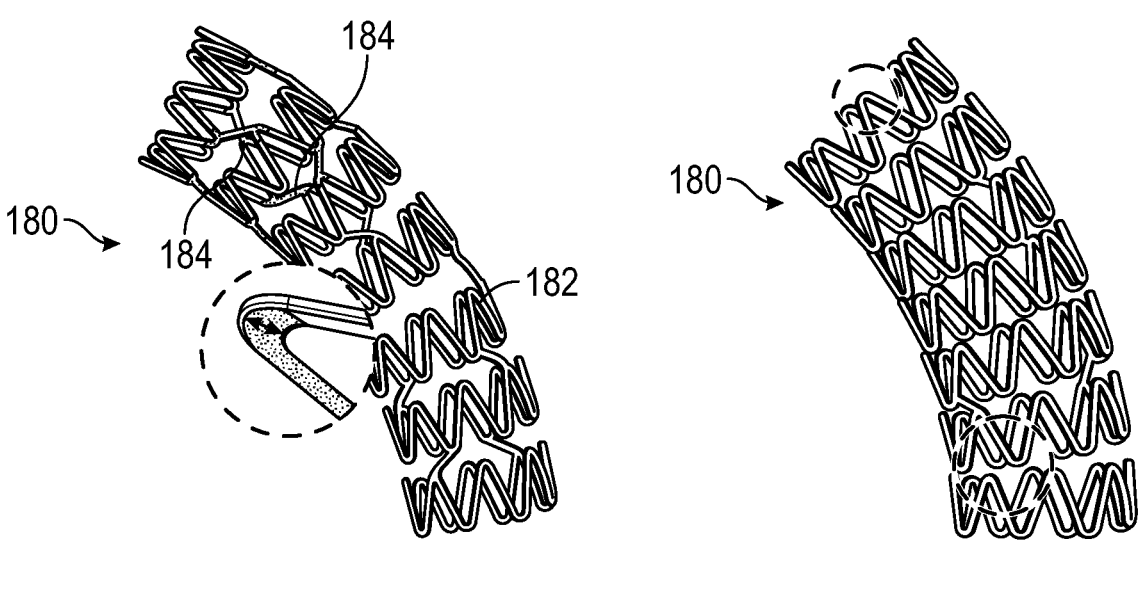
FIG. 10                FIG. 11

ARTHROPLASTY INSERT

CLAIM OF PRIORITY

This application claims the benefit of U.S. Provisional Patent Application Ser. No. 63/252,851, filed on Oct. 6, 2021, the benefit of priority of which is claimed hereby, and which is incorporated by reference herein in its entirety.

FIELD

The present subject matter relates to orthopedic procedures and, more particularly, to an insert for such orthopedic procedures.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. In a knee arthroplasty, a bearing component is attached to a tibial prosthesis and is contacted by a femoral prosthesis during kinematic movement of the knee joint.

Orthopedic surgeons currently use traditional instruments to perform knee replacement surgery (e.g., knee arthroplasty). The surgeon uses his best judgment to perform bone cuts and ligament releases based on his training, surgical skills, and experience. The surgeon aims at achieving post-surgical knee alignments that are closest to a guidance range for the population rather than customizing these measurements for each patient.

Orthopedic surgeons currently have the option of choosing between several standard bearing component designs. These include, but are not limited to a cruciate retaining design, a medial congruent design, an ultra-congruent design, and a posterior stabilized design. The orthopedic surgeon must choose one of these designs (of a proper size) that they think will provide the patient with a best possible range of motion and stability based upon parameters such as Posterior Cruciate Ligament ("PCL") quality, other ligament laxity, bone quality, range of motion, conformity, etc.

The process of selecting a desired bearing component can be time consuming and is ultimately a subjective decision by the orthopedic surgeon. While surgeons achieve the expected post-operative results in many cases, a significant number of patients remain dissatisfied post-operatively after an orthopedic procedure. This can be the result of various factors including the surgeon's subjective decisions. These decisions may be based upon a one-size-fits-all approach in total knee replacement that does not take into consideration preoperative patient function.

OVERVIEW

The present inventor recognizes, among other things, an opportunity for facilitating rapid and convenient in situ shape and/or size modification of an insert until desired joint kinematics (e.g., range of motion, stability, joint laxity, etc.) during an orthopedic procedure are achieved. The desired joint kinematics can be based upon objectively sensed criteria and can be personalized to the patient rather than being based upon subjective assessment by a surgeon. Thus, better outcomes and improved patient satisfaction can be achieved. More particularly, alteration in the shape and/or size of the insert can be controlled based upon feedback by one or more sensors and according to one or more control algorithms. A proximal surface of the insert can be manipulated in shape by the inflation or deflation of one or more bladders within the insert to achieve a desired conformity along a proximal surface thereof with the femoral implant.

The present inventor has also recognized that surgical complexity can be reduced by providing a system where the insert does not need to be trialed. Furthermore, various systems of differently sized and shaped standard tibial bearing component designs do not have to be carried as inventory.

Present day smart implants only collect data from an implanted sensor. However, such data is only used during intra-operative balancing of the joint of other patients to achieve kinematics using trialing of provisional components in future operations. Currently, implants, in particular the insert, are not modified for the patient receiving the implant in the post-op period based upon collected sensor data. The present application contemplates allowing the insert to configure a surface congruence (in any area on and on multiple surfaces of the insert) and other characteristics such as height, slope, anterior/posterior surfaces, medial pivot, expected knee valgus/varus, anterior-posterior translation and implant constraint. This would be based on sensor data collected from the joint post operatively. This would allow the patient's joint to move in the most natural manner by changing insert morphology based on joint kinematics.

To further illustrate the apparatuses, systems and methods disclosed herein, the following non-limiting examples (described as techniques below) are provided:

In some aspects, the techniques described herein relate to an insert for replacement of a joint of a patient, the insert including: a body having a plurality of bladders therein, two or more of the plurality of bladders in fluid communication with one another, the plurality of bladders expandable and contractible in volume; a proximal surface shapable by a change in the volume of one or more of the plurality of bladders, the proximal surface configured to interface with a first arthroplasty implant of the patient; and a distal surface spaced from the proximal surface by the body, the distal surface configured to interface with a second arthroplasty implant of the patient.

In some aspects, the techniques described herein relate to the insert, further including a central reservoir in selective fluid communication with the plurality of bladders, wherein the central reservoir has an inlet to receive a fluid therein from external of the insert.

In some aspects, the techniques described herein relate to the insert, further including one or more valves positioned in the body between the central reservoir and the plurality of bladders, the one or more valves regulating a flow of a fluid between the central reservoir and the plurality of bladders.

In some aspects, the techniques described herein relate to the insert, wherein at least the proximal surface is formed of a material that is shapable in situ.

In some aspects, the techniques described herein relate to the insert, wherein the material is a hydrogel membrane.

In some aspects, the techniques described herein relate to the insert, further including a scaffold positioned between one or more of the plurality of bladders and the proximal surface.

In some aspects, the techniques described herein relate to the insert, wherein the proximal surface is shapable to achieve one of a cruciate retaining design, a medial congruent design, an ultra-congruent design, a posterior stabilized design, another standard design or a hybrid design of the cruciate retaining design, the medial congruent design, the ultra-congruent design or the posterior stabilized design.

In some aspects, the techniques described herein relate to a system for a knee arthroplasty, the system including: a tibial implant configured to couple to a resected surface of a tibia; a femoral implant configured to couple to a resected surface of a femur; an insert positionable between the femoral implant and the tibial implant, the insert including: a body with a plurality of bladders therein, two or more of the plurality of bladders in fluid communication with one another, the plurality of bladders expandable and contractible in volume; and a proximal surface shaped by changes in the volume of one or more of the plurality of bladders, the proximal surface configured to interface with the femoral implant; a first plurality of sensors configured to be positioned between the tibial implant and the insert, the first plurality of sensors arranged to correspond in a position distal of the plurality of bladders; a second plurality of sensors coupled to one of the femoral implant or femur; processing circuitry; and a memory that includes instructions, the instructions, when executed by the processing circuitry, cause the processing circuitry to: receive first sensor data from the first plurality of sensors; receive second sensor data from the second plurality of sensors; determine, based upon the first sensor data and the second sensor data, one or more kinematics of a knee joint of a patient; and control the insert to expand or contract one or more of the plurality of bladders including to shape the proximal surface based upon the one or more kinematics.

In some aspects, the techniques described herein relate to the system, wherein the memory that includes the instructions, when executed by the processing circuitry, further cause the processing circuitry to: receive medical imaging data of the knee joint of the patient; and generate a functional digital twin model of the knee joint including the insert based on the first and second sensor data and the medical imaging data, the functional digital twin model simulating the one or more kinematics of the knee joint.

In some aspects, the techniques described herein relate to the system, wherein the memory that includes the instructions, when executed by the processing circuitry, further cause the processing circuitry to: receive a simulated surgical procedure selection, the simulated surgical procedure selection including at least one of a size of the insert or a shape of the proximal surface of the insert; generate a predicted one or more kinematics of the knee joint based on the simulated surgical procedure selection with the functional digital twin model; and generate an indication of the predicted one or more kinematics.

In some aspects, the techniques described herein relate to the system, wherein the memory that includes the instructions, when executed by the processing circuitry, further cause the processing circuitry to create a digital topography simulating a maximum range of motion with a desired constraint for a simulated proximal surface of the insert in the functional digital twin model.

In some aspects, the techniques described herein relate to the system, wherein the control of the insert to expand or contract one or more of the plurality of bladders by the processing circuitry is based upon a machine learning knee joint model.

In some aspects, the techniques described herein relate to the system, wherein the insert includes a centrally positioned reservoir and one or more valves positioned in the body between the reservoir and the plurality of bladders, the one or more valves are controlled by the processing circuitry to regulate a flow of a fluid between the reservoir and the plurality of bladders.

In some aspects, the techniques described herein relate to the system, wherein the one or more kinematics of the knee joint include one or more of an amount of translation of the femur with respect to the tibia, an amount of rotation of the femur with respect to the tibia, and an amount of force on the first plurality of sensors.

In some aspects, the techniques described herein relate to the system, wherein the one or more kinematics of the knee joint are used to create a digital topography simulating a maximum range of motion with a desired constraint for a simulated proximal surface of the insert.

In some aspects, the techniques described herein relate to the system, wherein at least the proximal surface of the insert is formed of a material that is shapable in situ and a scaffold forms a part of the body positioned between one or more of the plurality of bladders and the material.

In some aspects, the techniques described herein relate to the system, wherein the insert is configured to use synovial fluid of the knee joint of the patient as a fluid for the plurality of bladders.

In some aspects, the techniques described herein relate to a method for generating an arthroplasty functional digital twin, the method including: receiving first sensor data from a first plurality of sensors positioned between an insert and a first implant of a patient; receiving second sensor data from a second plurality of sensors implanted in the patient, the first sensor data and the second sensor data characterizing one or more kinematics of a musculoskeletal joint of the patient; receiving medical imaging data of the musculoskeletal joint; generating a functional digital twin model of the musculoskeletal joint including the insert based on the first sensor data, the second sensor data and the medical imaging data, the functional digital twin model simulating the one or more kinematics of a knee joint.

In some aspects, the techniques described herein relate to the method, further including generating a simulated surgical selection that includes altering at least one of a shape or a size of the insert in the functional digital twin model, the method further including: simulating the at least one or more of the shape or the size of the insert with the functional digital twin model; generating a predicted one or more kinematics of the musculoskeletal joint based on the simulating the at least one or more of the shape or the size of the insert with the functional digital twin model; and indicating the predicted one or more kinematics of the musculoskeletal joint.

In some aspects, the techniques described herein relate to the method, further including creating a digital topography simulating a maximum range of motion with a desired constraint for a simulated proximal surface of the insert in the functional digital twin model.

In some aspects, the techniques described herein relate to the method, further including altering at least one of a shape or a size of the insert in situ based upon the functional digital twin model.

In some aspects, the techniques described herein relate to the method, wherein the altering the at least one of the shape or size of the insert in situ includes controlling an amount of fluid within one or more of a plurality of bladders of the insert to expand or contract a volume of the one or more of the plurality bladders.

In some aspects, the techniques described herein relate to the method, wherein the altering the at least one of the shape or size of the insert in situ includes shaping a proximal surface of the insert using one or more of the plurality of bladders and a material shapable that alters shape in situ based upon a shape of the one or more of the plurality of bladders.

In some aspects, the techniques described herein relate to the method, wherein the shaping the proximal surface of the insert includes creating a digital topography simulating a maximum range of motion with a desired constraint for a simulated proximal surface of the insert.

In some aspects, the techniques described herein relate to machine-readable medium including instructions, which when executed by a computing system, cause the computing system to perform any of the previous techniques.

In some aspects, the techniques described herein relate to apparatus including means for performing any of the previous techniques.

In some aspects, the techniques described herein relate to systems to perform operations of any of the previous techniques.

In some aspects, the techniques described herein relate to an assembly for a knee arthroplasty, the assembly including: a tibial implant coupled to a resected surface of a tibia; a femoral implant coupled to a resected surface of a femur; an insert positioned between the femoral implant and the tibial implant and coupled to the tibial implant, the insert including: a body with a plurality of bladders therein, two or more of the plurality of bladders in fluid communication with one another, the plurality of bladders expandable and contractible in volume; and a proximal surface shaped by changes in the volume of one or more of the plurality of bladders, the proximal surface interfacing with the femoral implant; a first plurality of sensors positioned between the tibial implant and the insert, the first plurality of sensors arranged to correspond in a position distal of the plurality of bladders; a second plurality of sensors coupled to one of the femoral implant or femur; processing circuitry mounted to one of the tibial implant or the femoral implant; and a memory that includes instructions, the instructions, when executed by the processing circuitry, cause the processing circuitry to: receive first sensor data from the first plurality of sensors; receive second sensor data from the second plurality of sensors; determine, based upon the first sensor data and the second sensor data, one or more kinematics of a knee joint of a patient; and control the insert to expand or contract one or more of the plurality of bladders including to shape the proximal surface based upon the one or more kinematics.

In some aspects, the techniques described herein relate to the assembly, wherein the insert includes any one or combination of the foregoing.

These and other examples and features of the present apparatuses and systems and method will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIGS. 9-11 show various examples of a scaffold that can be utilized with the insert of FIG. 8 according to an example of the present application.

DETAILED DESCRIPTION

The present application relates to prostheses, method and systems that can be used in various orthopedic replacement procedures (arthroplasties). Although discussed in respect to a particular knee replacement procedure, a total knee arthroplasty (TKA), the concepts and systems can be used in other joints of the human body including the ankle, hip, shoulder, brain and/or spine, for example. Furthermore, the prostheses, method and systems discussed herein are not limited to the TKA but, to other knee replacement procedures (e.g., partial knee replacements such as unicompartmental procedures, revision knee replacement procedures, etc.).

The disclosed apparatuses include a tibial bearing component. This document refers to this tibial bearing component as an insert. According to some examples, the insert can be affixed to a tibial baseplate (also called a tibial prosthesis, tibial baseplate or tibial implant herein). As further discussed herein the insert can be shape and/or size altered in situ via a control algorithm and based upon sensor feedback to achieve desired joint kinematics.

Although not specifically illustrated, it is understood the insert can have a connection mechanism that is employed to fix the insert to the tibial baseplate. According to some examples, the connection mechanism can include a dovetail boss on the tibial baseplate cooperating with a corresponding notch on the insert, a peripheral rail of the tibial baseplate cooperating with a corresponding recessed portion of the insert, a pair of anterior wedges projecting from an anterior edge of the insert that cooperate with an undercut within an anterior peripheral rail of the tibial baseplate, a bond or over-mold of the insert to the tibial baseplate, any combination of these features, or other fixation mechanism known in the art. However, the disclosed interaction between the bearing and the insert can be that of a mobile bearing application as the bearing articulates with respect to the insert (such as by sliding or rotating) along a desired motion path over the insert.

As used herein, "proximal" refers to a direction generally toward the torso of a patient, and "distal" refers to the opposite direction of proximal, i.e., away from the torso of a patient. As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior". Similarly, the terms "medial" and "lateral" should be given their generally understood anatomical interpretation. "Medial" refers to the opposite direction of "lateral".

Figure 1:
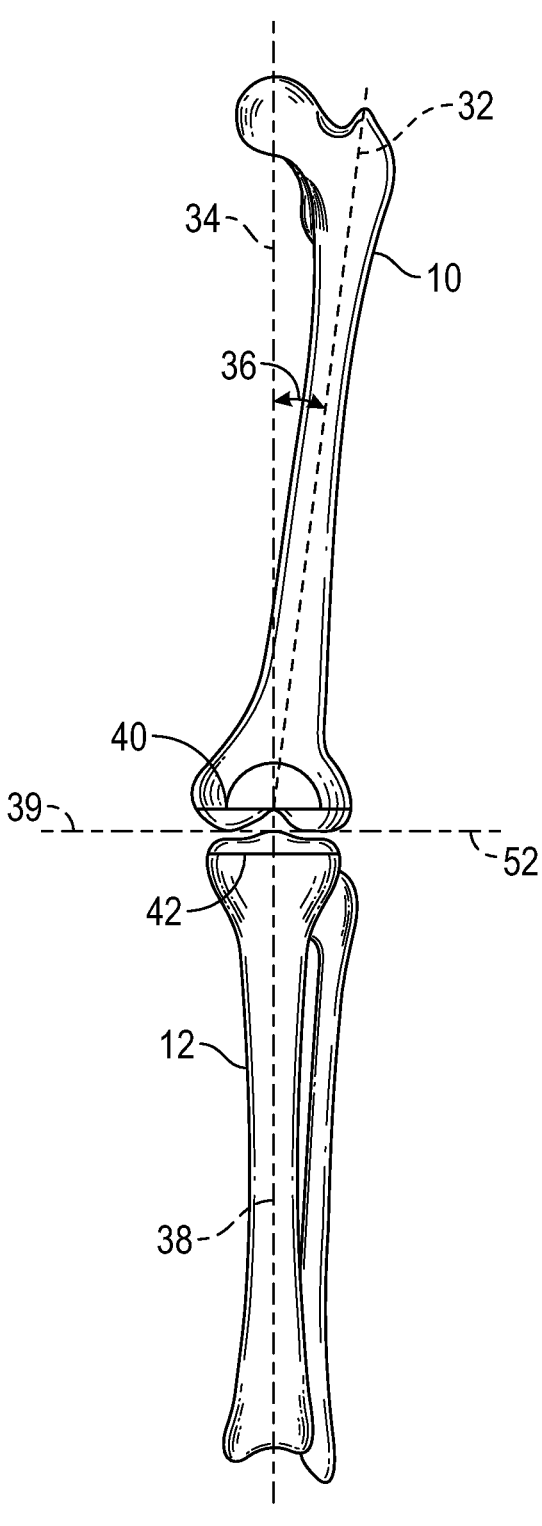
FIG. 1 is a front elevation view of a tibia and a femur showing axes of the knee joint according to example of the present application.

FIG. 1 illustrates a natural femur 10 and tibia 12 and illustrates several aspects relevant to prosthesis orientation. FIG. 1 illustrates various axes of the lower limb in the frontal plane. Axes can be defined for each segment of the lower limb. For example, the femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane. Likewise, the tibia 12 has a mechanical axis 38 coinciding generally with its intramedullary canal. The mechanical axis 38 of the tibia 12 runs from the center of the knee to the center of the ankle. The transverse axis, or joint line 39, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

The distal femoral cut is typically made perpendicular to the femoral axes 32, 34 in the sagittal plane. The proximal tibial resection is typically cut to match the natural posterior slope, or rotation, of the proximal tibia relative to the mechanical axes 34, 38. The amount of posterior to anterior slope (i.e. the change of resection 42 anterior to posterior relative to a reference line 52 perpendicular to the mechanical axes 34, 38 varies in the patient population but is on the order of 5° to 7°). Other cuts may be made depending on the components that are to be implanted.

Figure 2:
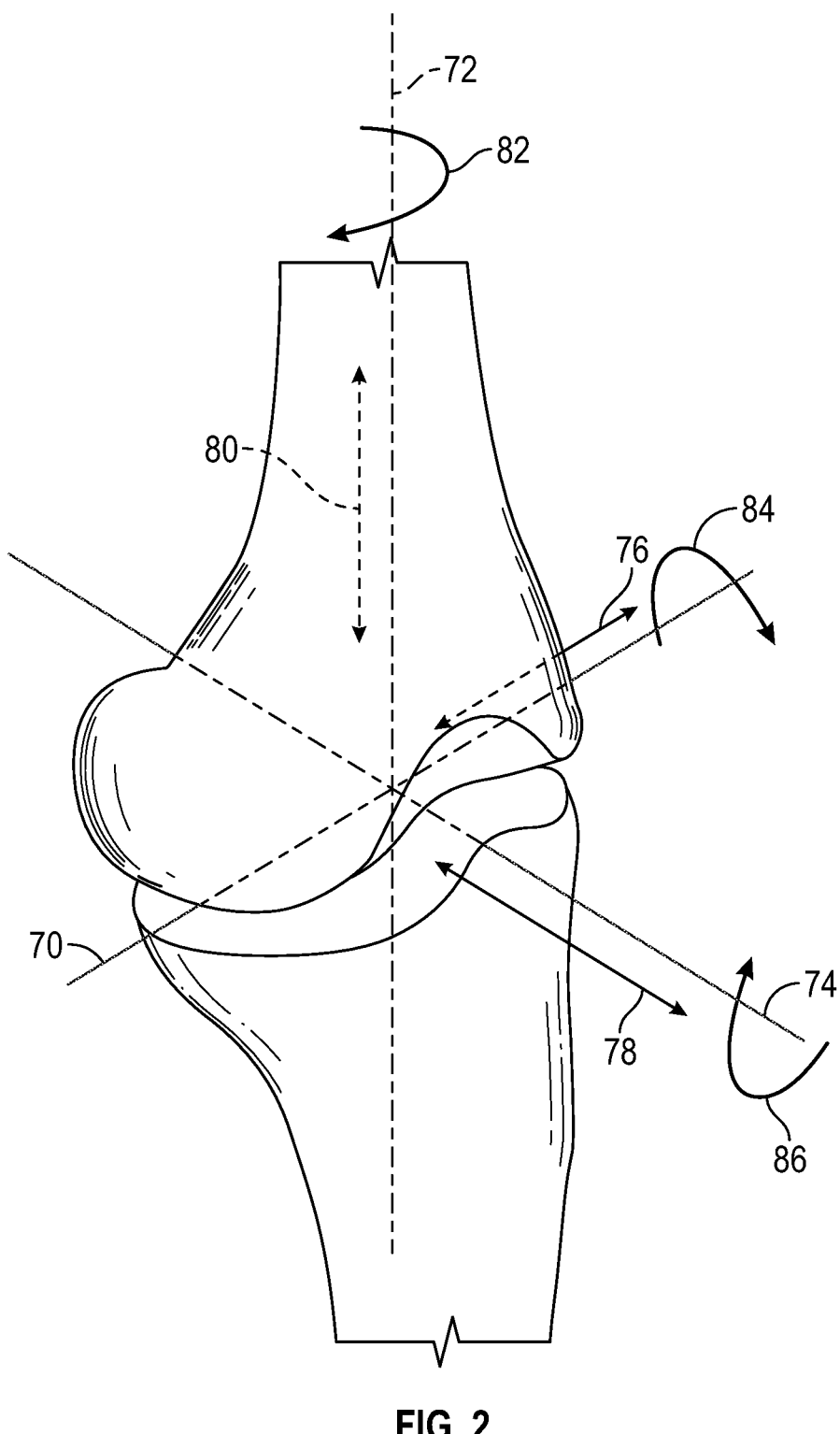
FIG. 2 is a perspective view of knee joint showing aspects of some knee joint kinematics according to example of the present application.

FIG. 2 depicts six aspects of component positioning relative to a coordinate system in which the x-axis 70 corresponds approximately to the joint line 39, the z-axis 72 corresponds approximately to the mechanical axes 34 and 38, and the y-axis 74 is normal to the other two. Position along each of these axes is depicted by arrows. Position along the x, y, and z axes determines the medial/lateral (dx) 76, anterior/posterior (dy) 78, and proximal/distal (dz) 80 positioning of components respectively. Rotation about each of these axes is also depicted by arrows. Rotation about the z-axis (rz) 82 corresponds anatomically to external rotation of the femoral component, rotation about the x-axis (rx) 84 corresponds to extension plane rotation, and rotation about the y-axis (ry) 86 corresponds to varus/valgus rotation.

Figure 3:
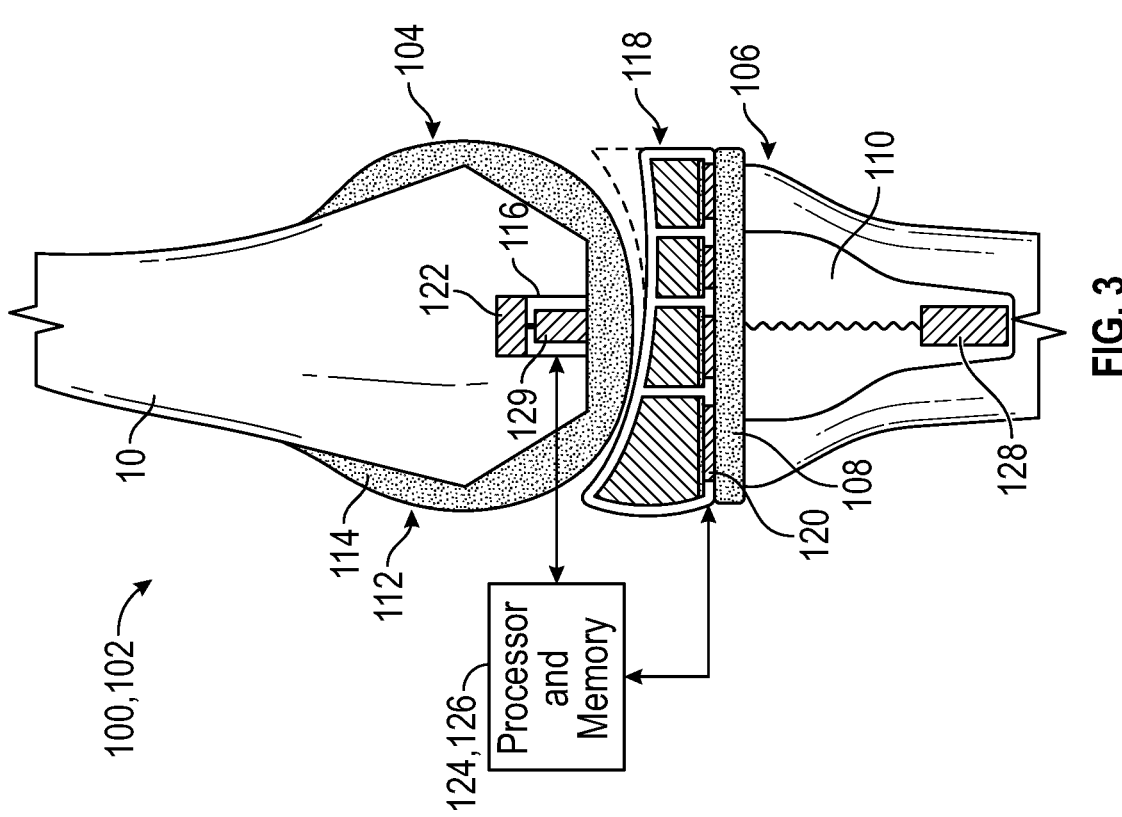
FIG. 3 is a cross-sectional sagittal view of a knee joint of a patient including a system having a tibial implant, a femoral implant and an insert according to example of the present application.

FIG. 3 shows a system 100 according to an example of the present application. The system 100 can be an assembly 102 once mounted within a patient's knee joint 104. The system 100 can include a tibial prosthesis 106 (e.g., a tibial baseplate 108 and a keel 110), a femoral prosthesis 112 (e.g., a condylar body 114 and pegs 116), an insert 118, a first plurality of sensors 120, a second plurality of sensors 122, processing circuitry 124 and a memory 126.

The tibial prosthesis 106 can be mounted to a resected proximal surface of the tibia 12. Although illustrated as having a keel 110, according to further embodiments the tibial prosthesis 106 could have pegs or other distal fixation features as known in the art. The keel 110 can contain a battery 128 that can electrically power the first plurality of sensors 120 and other components of the system as further discussed herein.

The femoral prosthesis 112 can be mounted on the femur 10 with the condylar body 114 interfacing with and articulating with the insert 118 along condyles thereof. Although the femoral prosthesis 112 is illustrated with pegs 116 (only one peg is shown in FIG. 3), the femoral prosthesis 112 could utilize a keel or other fixation structure as known in the art according to further embodiments. Thus, the tibial prosthesis 106 and/or femoral prosthesis 112 could be cemented or uncemented.

The pegs 116 can house the second plurality of sensors 122 according to some embodiments. The pegs 116 can additionally house one or more batteries 129 that can electrically power at least the second plurality of sensors 122. Although FIG. 3 shows the second plurality of sensors 122 as coupled to the femoral prosthesis 112, it is contemplated the second plurality of sensors 122 could be separate therefrom, (e.g., inserted in to a medullary or other cavity of the femur 10) for example. According to further examples, the pegs 116 may not be utilized in favor or a keel or other distal fixation structure.

Figure 15:
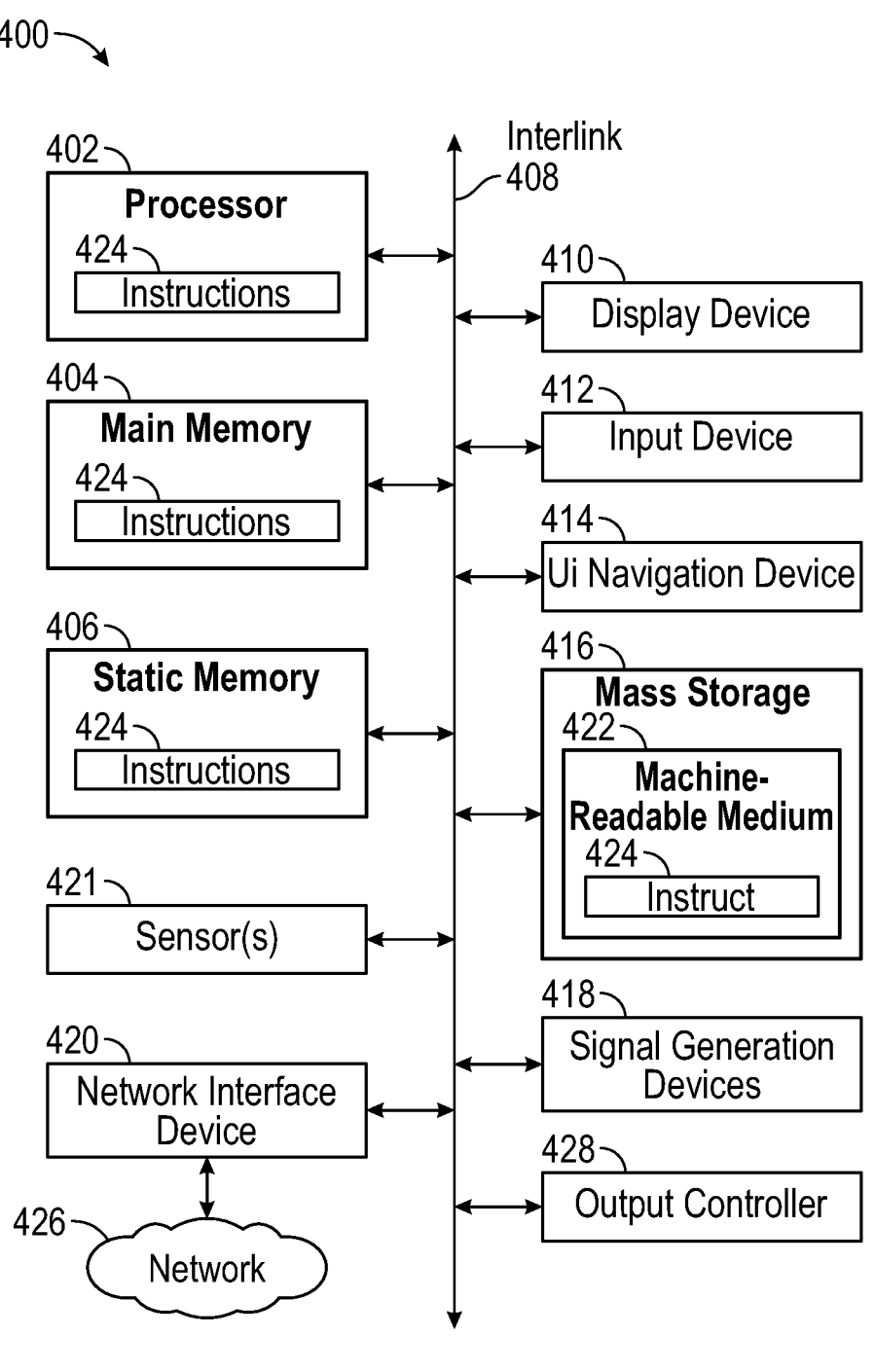
FIG. 15 illustrates an example of a block diagram of a machine upon which any one or more of the techniques discussed herein may perform according to another example of the present application.

The first plurality of sensors 120 and the second plurality of sensors 122 can communicate electronically (e.g., via wireless modality) with one another and/or with the processing circuitry 124. The processing circuitry 124 and/or memory 126 could be remote from the knee joint 104 or could be housed on a microchip or other processor device within the knee joint 104 (e.g., mounted on the femoral prosthesis 112, insert 118 and/or tibial prosthesis 106). FIG. 15 discusses various examples of the processing circuitry 124, memory 126 and other devices.

The insert 118 can be positioned between the femoral prosthesis 112 and the tibial prosthesis 106. The insert 118 can be coupled to the tibial prosthesis 106 as previously described. The insert 118 can be contacted along a proximal surface thereof by the femoral prosthesis 112 during articular movement of the knee joint 104. The first plurality of sensors 120 can be located proximal of the tibial prosthesis 106 between the insert 118 and the tibial prosthesis 106. For example, the first plurality of sensors 120 can be positioned on a surface of the tibial baseplate 108 or can be recessed slightly within the tibial baseplate but exposed.

As discussed, insert 118 can be configured to change shape and/or size in situ with feedback from the first plurality of sensors 120, the second plurality of sensors 122 and/or the processing circuitry 124. This methodology will be discussed in further detail subsequently.

Although the system 100 is described in reference to the tibial prosthesis 106 and the femoral prosthesis 112, it is contemplated in some examples that one or both of these implant components may not be utilized, (e.g., insert could be utilized on its own or with a single implant).

The second plurality of sensors 122 can include gyroscope(s) and/or accelerometer(s), for example. The second plurality of sensors 122 can communicate electronically to provide second sensor data with one another, with the processing circuitry 124 and/or with the first plurality of sensors 120 as further described herein. The first plurality of sensors 120 can comprise gyroscope(s), accelerometer(s), force and/or pressure sensors, for example. The first plurality of sensors 120 can communicate electronically with one another to provide first sensor data, with the processing circuitry 124 and/or with the second plurality of sensors 122 as further described herein. The sensors may be used to characterize the joint, such as by sensing force, pressure, position, motion, strain, torque, torsion, or other joint sensor information.

Figure 4A:
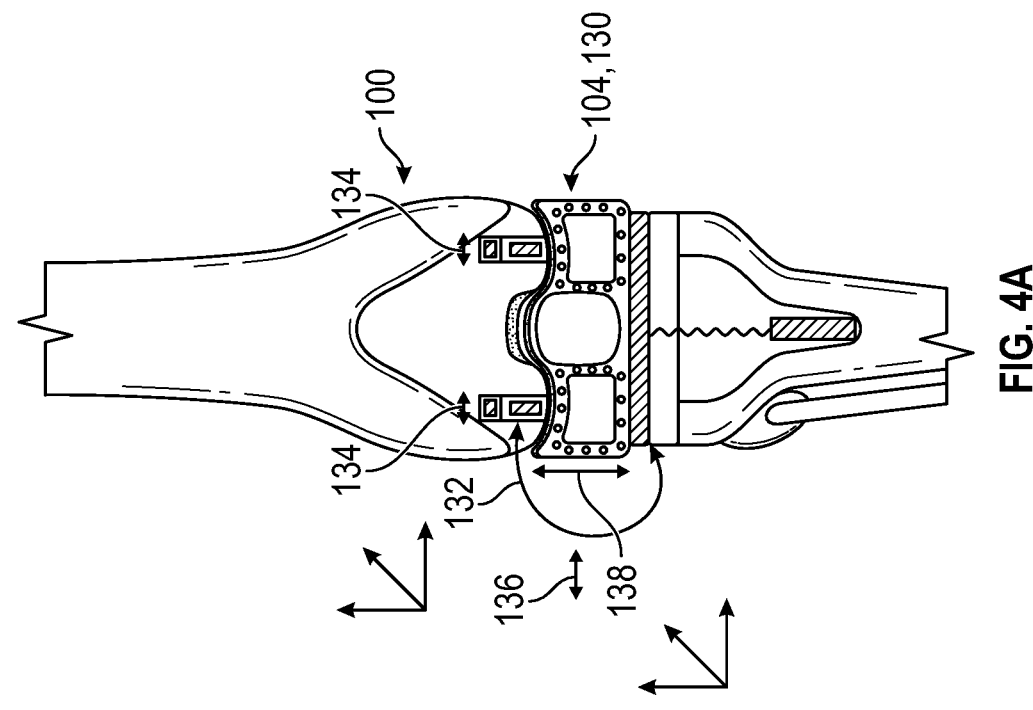
FIG. 4A is a cross-sectional frontal view of the knee joint of the patient with the system of FIG. 3 undergoing various movements indicated by arrows according to example of the present application.
Figure 5:
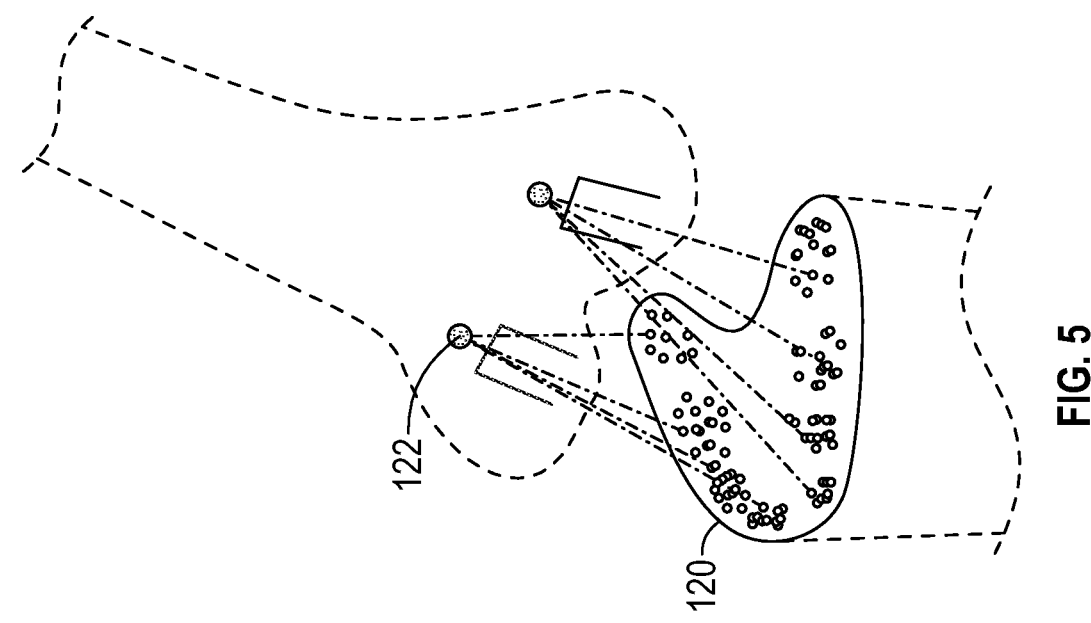
FIG. 5 is a schematic view of knee joint showing sensors communicating with one another according to an example of the present application.
Figure 4B:
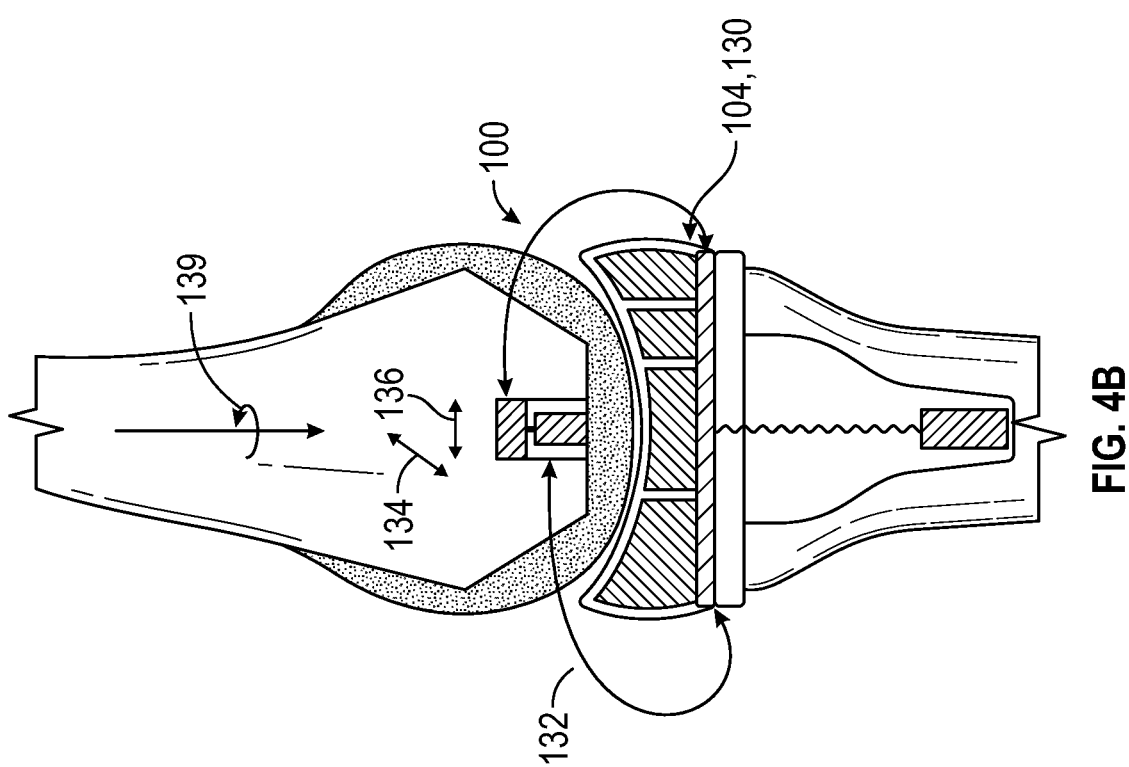
FIG. 4B is a cross-sectional sagittal view of the knee joint of the patient with the system of FIG. 3 undergoing the various movements indicated by arrows according to example of the present application.

FIGS. 4A, 4B and 5 show operation of the system 100 to capture data regarding various kinematics 130 of the knee joint 104 once the system 100 has been implanted. As shown variously in FIGS. 4A and 4B, the kinematics 130 include range of motion 132 of the knee joint 104 (e.g., from flexion to extension), medial-lateral translation 134, anterior-posterior translation 136, joint laxity 138 (measured by pressure or force on the first plurality of sensors 120), femoral rotation 139 (FIG. 4B), conformity (related to stability) etc.

FIG. 5 shows the first plurality of sensors 120 can communicate with the second plurality of sensors 122 and/or with the processing circuitry 124 (FIG. 3). The first plurality of sensors 120 (tibial baseplate sensors) can also communicate with the second plurality of sensors 122 constantly to collect various data points on the implant and the knee kinematics.

Figure 6A:
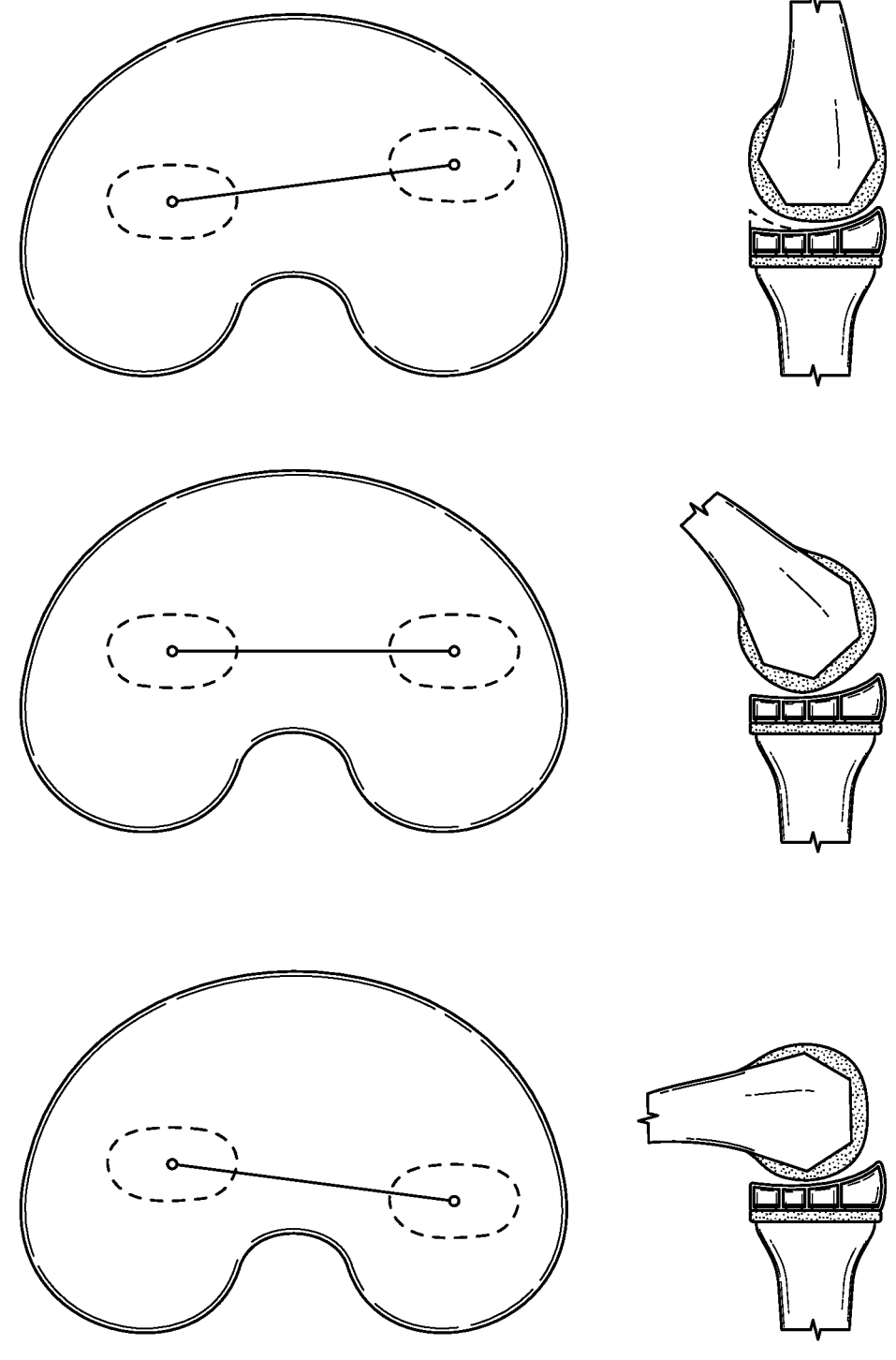
FIGS. 6A and 6B are schematic illustrations of various contact areas sensed by the sensors of FIGS. 4A-5 according to example of the present application.
Figure 6B:
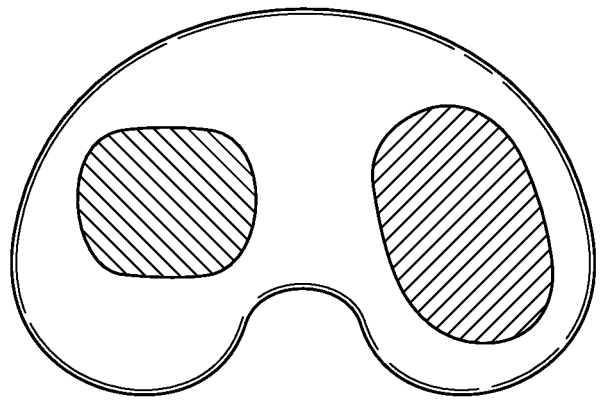

FIGS. 6A and 6B show various contact maps that can be generated through the range of motion of the knee joint from full flexion to full extension. The contact maps can be digital topographical renderings of the contact surface(s) between the proximal surface of the insert and the femoral prosthesis. The forces generated during flexion-extension range of motion of the knee joint and the medial pivot with anteroposterior translation of the various contact surfaces of the femur with the insert's proximal surface are mapped in every degree of range of motion (this is done with the sensors discussed herein). When the various points of contact and forces are registered a digital topography can be created in a 2-D or 3D image that shows the range within which the contact surfaces articulate when the knee is in range of motion. This technique is referred to as digital topography mapping of the contact surfaces of the femoral prosthesis on the insert. The contact surfaces then help to map the areas where more constraint is desired and/or not desired (i.e., less constraint is desired) allowing for a more balanced knee permitting maximum range of motion within the confines of the post-op anatomy given a desired level of constraint appropriate for the individual patient. FIGS. 6A and 6B show visually the digital topography superimposed on the proximal surface that results from some of the kinematics of the knee joint (e.g., a flexion-extension of the knee joint through a full range motion with a desired constraint determined to be optimal given the desired range of motion). FIG. 6A shows the topographical digital image through translation of the knee joint (both anterior/posterior and medial lateral) along with desired stability/constraint as dictated by congruence of the femoral prosthesis articular surface with the insert's proximal surface. The digital topographical images of FIG. 6A can create the further contact surface map of FIG. 6B that shows the contact area from full flexion to full extension. Sensors (e.g., the first plurality of sensors 120 and/or the second plurality of sensors 122 of FIG. 5) can map out the contact surfaces and can create the full flexion to extension topographical map as shown in FIG. 6B. At each degree of flexion to extension various kinematics such as translation of components, medial/lateral movements, rotation of femur, force(s), pressure(s), acceleration (s), vector and other criteria can be measured by the sensors and are captured by the digital topography.

Figure 7:
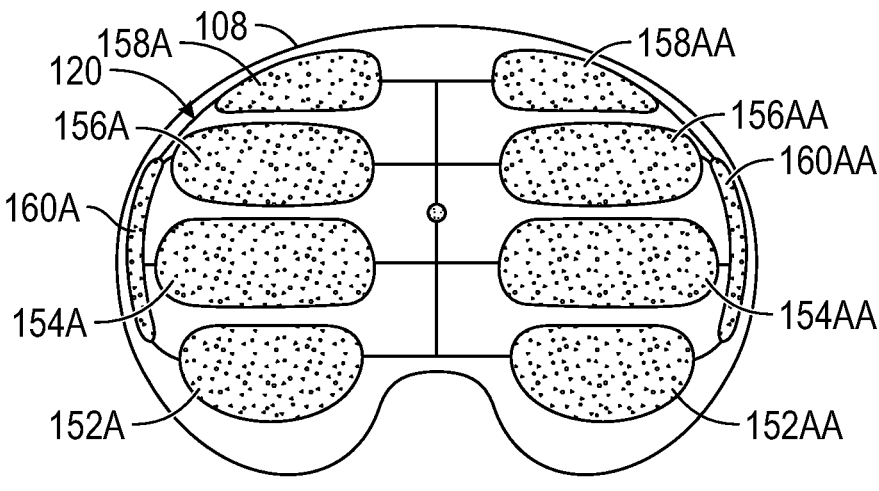
FIG. 7 is an elevated plan view from a proximal side of the tibial implant showing a plurality of sensors placed thereon according to example of the present application

FIG. 7 shows the first plurality of sensors 120 and the tibial baseplate 108 in further detail. The tibial baseplate 108 can be constructed in a manner as known in the art (e.g., using titanium alloy and having keel, proximal surface, periphery wall and other fixation features). The plurality of sensors 120 can be mounted on the proximal surface of the tibial baseplate 108, for example. The first plurality of sensors 120 can have a central connection to a power source (e.g., the battery 128 of FIG. 3) in the tibial keel. The power source communication can be provided through this central connection to the various sensors. The first plurality of sensors 120 to be on the medial, lateral, anterior and/or posterior sides of the tibial baseplate 108. Various configurations of sensors can be used. In the configuration shown in FIG. 7, the tibial baseplate 108 can be divided into medial and lateral columns. There can be four sensor groups 152A, 152AA, 154A, 154AA, 156A, 156AA and 158A, 158AA on each of the medial and lateral sides. Each of these sensor groups can be a pad with multiple sensors arranged thereon. These sensor groups 152A, 152AA, 154A, 154AA, 156A, 156AA and 158A, 158AA can be arranged to correspond/ match and be contacted by features on the insert 118 (FIG. 3) as further discussed. In particular, the sensor groups 152A, 152AA, 154A, 154AA, 156A, 156AA and 158A, 158AA can be directly distal of a plurality of bladders of the insert as further discussed and illustrated in FIG. 8.

As shown in FIG. 7, there are also lateral and medial edge sensors 160A and 160AA. A posterior sensor could also be added to collect data from the posterior aspect of the tibial baseplate 108 and insert 118 if desired. The first plurality of sensors 120 can communicate with each other, with the second plurality of sensors 122 and a processor/circuit as previously discussed. The first plurality of sensors 120 can be gyroscopes, accelerometers, pressure sensors and/or force sensors or the like.

As discussed previously, the tibial baseplate 108, insert 118 (FIG. 3) or another component could be configured to house a processor (e.g., a microchip). The processor could be powered by the same power source from the tibial baseplate 108 (e.g., battery 128 of FIG. 3) and the processor can process the first sensor input data gathered by the first plurality of sensors 120 and/or the second sensor input data gathered by the second plurality of sensors 122. A transmitter and input receiver could be utilized and would permit sending and receiving all sensor input data and input commands (electronic control signals) in order to control the insert shape and/or size as further discussed herein.

Figure 8:
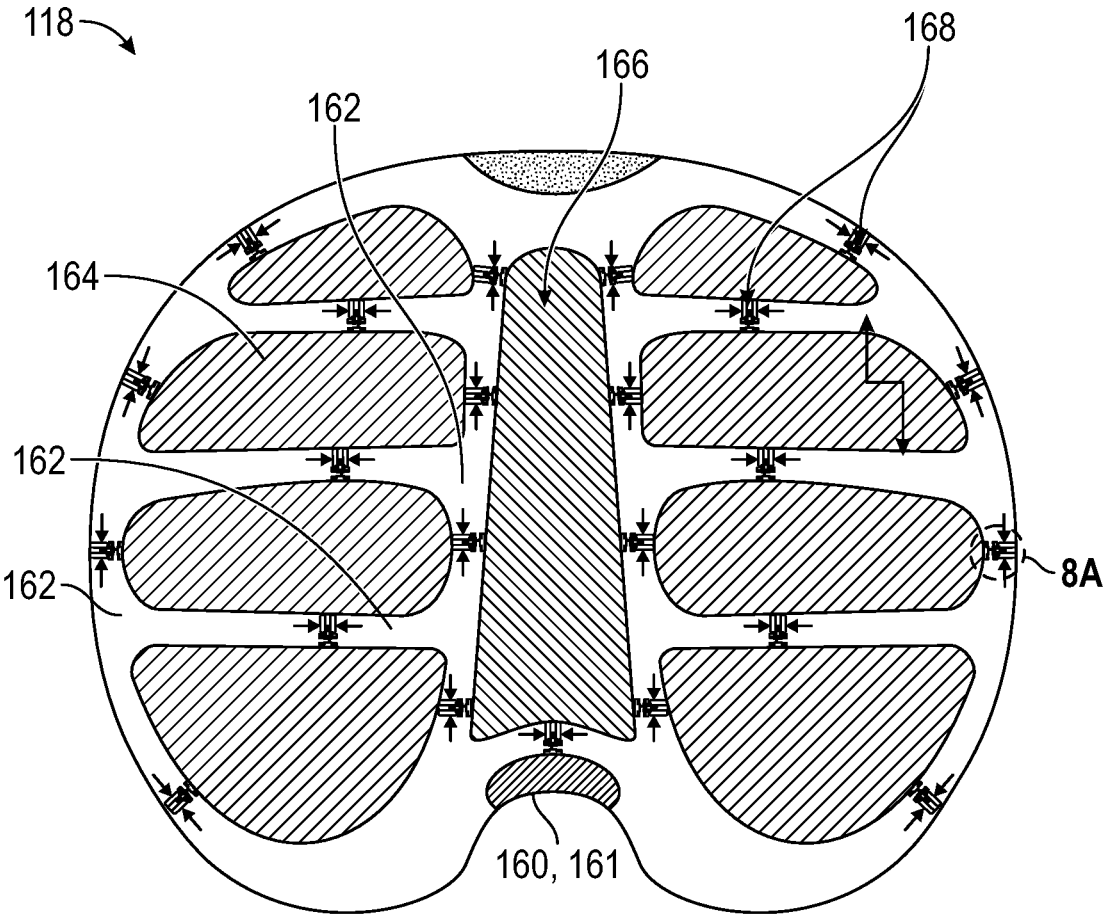
FIG. 8 is a cross-sectional view in a transverse plane of the insert having a plurality of bladders, a reservoir and other features according to an example of the present application.

FIG. 8 shows an example of the insert 118. The insert 118 can include a base 160, one or more walls 162, a plurality of bladders 164, a reservoir 166 and one or more valves 168.

The insert 118 can mirror the tibial baseplate 108 (FIG. 7) in shape. The insert 118 can have a sensor electronic connection and/or a control electronic connection if desired. This connection can be a wireless connection or wired connection according to various examples. Furthermore, the insert 118 can have a power connection such as with the battery of the tibial component.

The insert 118 can have a solid non-in situ shapable polymer that forms the base 160 (which includes a distal surface 161 (FIG. 8) and the one or more walls 162, such as for the medial, lateral, anterior and posterior peripheral sides and in a central intercondylar area. Suitable polymer(s) for the insert 118 are known in the art and are currently in use for tibial bearing components. This solid non-in situ shapable structure will give the insert 118 a desired shape along the one or more walls 162 that form the periphery and the base 160 thereof and can prevent the insert 118 from deforming in these directions.

Figure 8A:
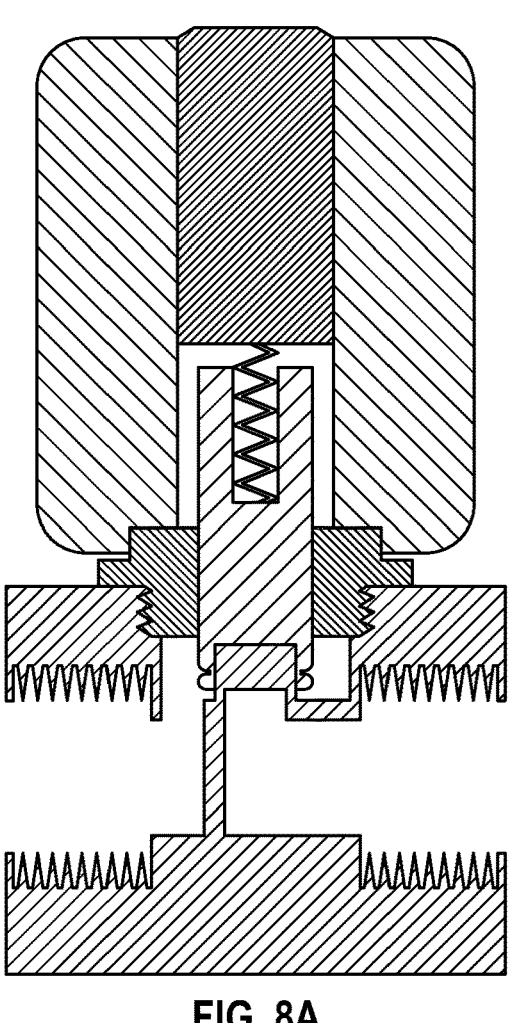
FIG. 8A is an enlarged view of one of a plurality of valves of the insert according to an example of the present application.
Figure 8B:
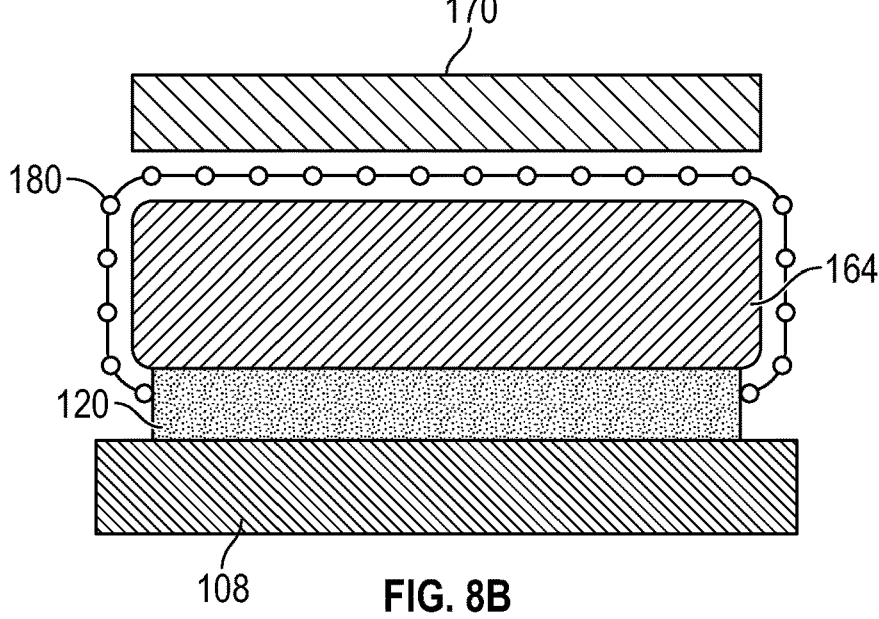
FIG. 8B is an enlarged cross-sectional view of the insert through one of the plurality of bladders according to an example of the present application.
Figure 12:
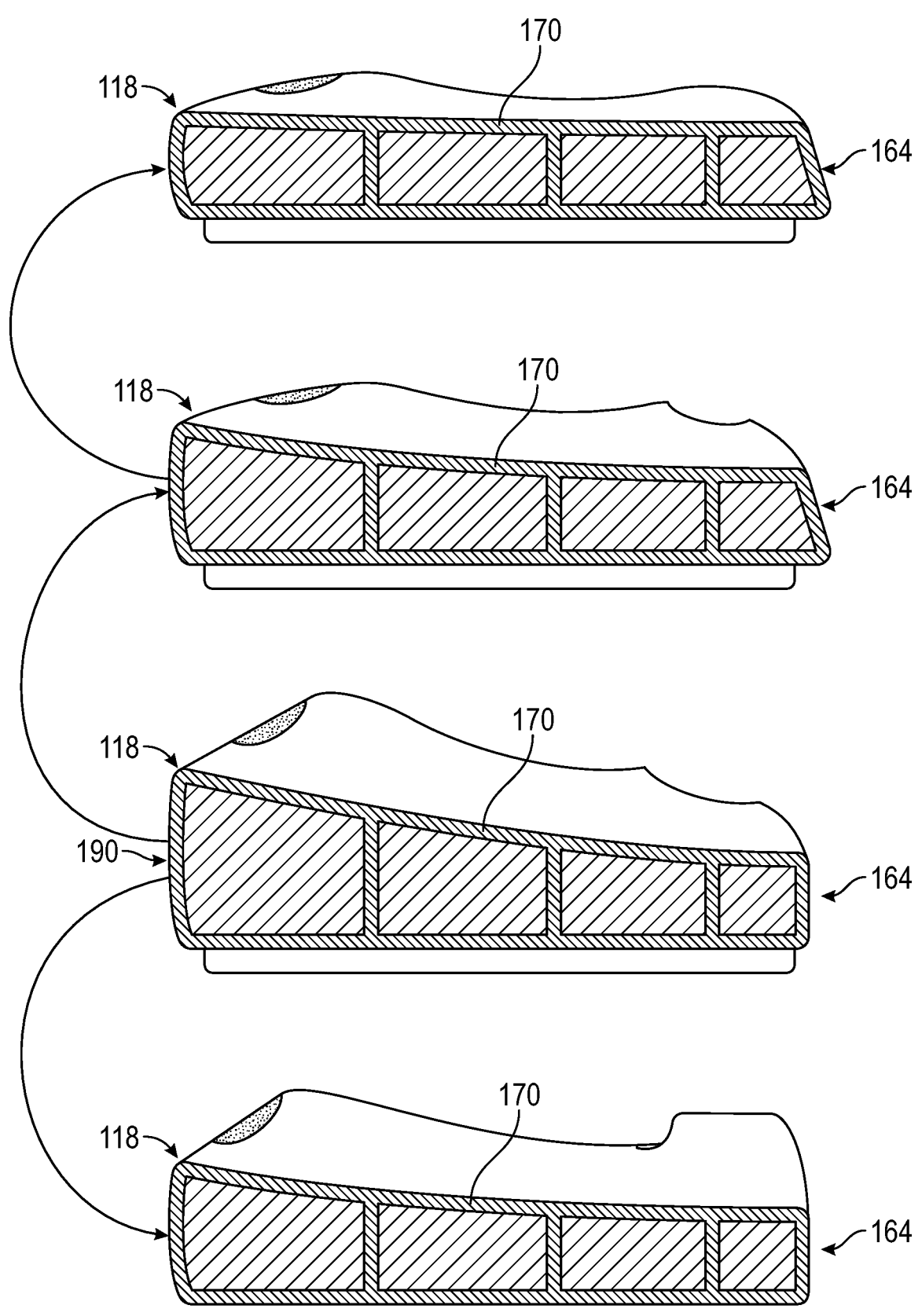
FIG. 12 shows various cross-sectional views of different possible insert designs that can be achieved in situ according to an example of the present application.

As shown in FIGS. 8B and 12, a proximal surface 170 (e.g., the contact surface with the femoral component) of the insert 118 can be made from a shapable and/or mouldable material that can deform in situ. This material can be a hydrogel or hydrogel membrane for example. Such hydrogel can include, but is not limited to a Kevlar® based cartilage, Kevlartilage™, or the like. The material could have a high tensile strength so as to be shaped in situ without breaking or cracking due to the various forces of the knee joint and/or internal hydrodynamic forces.

The reservoir 166 can be located in a central intercondylar portion between the femoral condyles. The reservoir 166 can comprise a central chamber that can be a high pressure isotonic fluid holding chamber. Contemplated fluids utilized can include, but is not limited to: synovial fluid of the knee joint, isotonic saline solution, 5% dextrose solution (other part isotonic saline, water or another constituent) Lactated Ringer's solution in 5% dextrose solution, 100% Lactated Ringer's solution. The reservoir 166 can fluidly communicate with the plurality of bladders 164. Two or more of the plurality of bladders 164 can additionally be in fluid communication with one another as shown in FIG. 8.

The reservoir 166 can hold the fluid under a higher pressure than a pressure of the plurality of bladders 164. The plurality of bladders 164 can be constructed of the shapable material (e.g., hydrogel, hydrogel membrane, etc.) similar to or identical to the material of the proximal surface 170 (FIG. 12). Thus, the plurality of bladders 164 can be expandable and contractible (i.e., can be inflated or deflated) having an internal cavity that changes in volume by receiving more or less of a volume of the fluid such as from the reservoir 166. The plurality of bladders 164 can surround the reservoir 166.

According to one example, fluid passages exist between the reservoir 166 and the plurality of bladders 164, between certain of the plurality of bladders 164, and between one or more of the plurality of bladders 164 and external to the insert. These fluid passages can have one or more valves 168 therein. These one or more valves 168 can regulate flow to/from the plurality of bladders 164 from the reservoir 166 and can regulate a flow of the fluid between the plurality of bladders 164 into/out of the plurality of bladders 164 from external of the insert 118 in the knee joint.

According to one example, the one or more valves 168 can comprise solenoid valves 172 (or another type of valve known in the art) that can be electronically controlled to open or close as desired according to a control scheme or algorithm as implanted by the control circuitry on the processor or another medium as discussed herein. For example, as shown in FIG. 8A, the one or more valves 168 can be direct operated solenoid valves 172 that are powered through the tibial prosthesis power source (i.e., the battery 128 of FIG. 3) connected through the tibial baseplate and insert 118. These direct operated solenoid valves 172 can be as small as 1 mm in size and can regulate the flow of the fluid including from reservoir 166 to the plurality of bladders 164, between the plurality of bladders 164 and/or from external to the insert 118 into/out the plurality of bladders 164 and/or reservoir 166 to the knee. Upon initial insertion of the insert 118 in situ between the femoral prosthesis and the tibial prosthesis, the plurality of bladders 164 can be in an original configuration, in which all the plurality of bladders 164 contain tonic fluid solution and the plurality of bladders 164 can be inflated with maximum volume of fluid so as to achieve a maximum size.

Once the insert 118 is placed in situ into position, one or more assessments to determine the joint kinematics previously illustrated in FIGS. 4A-6B can be carried out. Based upon data from the first plurality of sensors 120 and/or second plurality of sensors 122 (FIG. 3) control signals can be sent to the one or more valves 168 regulating the volume of the plurality of bladders 164. These one or more valves 168 can open and close to regulate the fluid pressure in the plurality of bladders 164 as desired. In most cases, a volume of the fluid will get pushed from the plurality of bladders 164 out of the insert 118 into the knee joint and will later get absorbed from the knee's synovial fluid system. In the future, if a need develops to further increase a volume of fluid in one or more of the plurality of bladders 164 to increase the size of the one or more of the plurality of bladders 164 to alter shape of the proximal surface 170 (FIGS. 8B and 12) the one or more valves 168 can be opened to push in high pressure fluid from the reservoir 166 to the one or more of the plurality of bladders 164. This can alter bladder shape as desired such as determined by the controller. The one or more valves 168 could also be selectively opened such as to external of the insert 118 if further reduction in pressure is needed. With the one or more valves 168 opened fluid pressure can push the fluid out of the one or more of the plurality of bladders 164 and into the knee joint. The reservoir 166 can have an inlet and can receive further volume of fluid therein for example via an injection if desired. Fluid could also be injected directly into one or more of the plurality of bladders 164 as desired.

In this manner, a customized shape of the insert 118 in situ can be obtained based on sensor data (e.g., from the first and/or second plurality of sensors of FIG. 3) collected and based on the final implant component positions within the knee joint obtained post-operatively. Such sensor data can be collected in real-time or batched, packaged or otherwise obtained. This shape for the insert 118 can be better than three-dimensional printed models because the insert 118 is not based computer simulations but based on actual patient-specific sensor data determined after all implant components and ligament releases are done and in the post-operative period.

According to some examples, the fluid utilized for the insert can be synovial fluid captured from the knee joint itself as previously discussed. In such case, a device such as a compressor, pump etc. may need to be utilized to increase the pressure of the synovial fluid and/or pump the synovial fluid into one or more of the plurality of bladders 164 internal chamber(s).

According to further examples, should a permanent shape solution (i.e. once the insert shape has reached optimum based upon collected sensor data and controller analysis) be desired, a high pressure binding agent could be pumped from the reservoir into the plurality of bladders 164 (e.g., an Araldite-like biocompatible substance, bone cement or two or more other biocompatible substances where when the two substances are mixed the initial two fluids solidify). This configuration would allow for a customized permanent shape creation of the insert 118 in situ of the patient based on the sensor data collected as discussed previously.

If the insert design is not needed to be solidified and the central reservoir chamber is empty (such as after initial or subsequent shaping of the insert has been performed) and the insert needs to be reshaped then the reservoir 166 can be recharged by injecting isotonic solution(s) or even the patient's synovial fluid (drawn by the surgeon). This fluid can be pressure injected from outside into the insert. A small radiopaque bead can be placed at this entry point into the insert's recharging reservoir 166 to allow the surgeon to view the insert 118 under X-ray to control and place the injector mechanism to recharge the reservoir 166.

FIG. 8B shows a cross-sectional view of the insert 118 through one of the plurality of bladders 164 and additionally shows the tibial baseplate 108 and one of the first plurality of sensors 120. FIG. 8B shows the insert 118 can include the proximal surface 170 (e.g., formed of hydrogel, hydrogel membrane or other shapable material), a scaffold 180 and the one of the plurality of bladders 164.

The scaffold 180 can be constructed of suitable material (s) such as metal, metal alloy, etc. The scaffold 180 can be arranged around only a portion of the one of the plurality of bladders 164 such as around three sides including between the one of the plurality of bladders 164 and the proximal surface 170. The scaffold 180 may not extend between the one of the plurality of bladders 164 and the one of the first plurality of sensors 120 such that they are in direct contact with one another. The scaffold 180 can be arranged in several connected layers, for example.

FIGS. 9-11 illustrate further examples for the construct of the scaffold 180. The scaffold 180 can act as a skeleton to support the expandible plurality of bladders 164 (e.g., as shown in FIG. 8B). The scaffold 180 can extend over a top of the plurality of bladders 164 (again as shown in FIG. 8B) and can be constructed in a similar manner to a cardiac stent. However, meshes of the scaffold could be made of tensile metal/metal alloy that could be easily deformed. However, it may be desirable that the scaffold 180 could also have a recoil effect as such effect could allow the scaffold 180 to modulate the shape of the insert 118 (if pressure is increased to one or more of the plurality of bladders 164 the shape of the insert 118 will change (e.g., the size of the insert 118 including the one of the plurality of bladders 164 and scaffold 180 will expand in volume). Similarly, if the pressure within the one of the plurality of bladders 164 is reduced the shape if insert 118 will change (e.g., the size of the insert 118 including the one of the plurality of bladders 164 and scaffold 180 will contract in volume).

FIGS. 9-11 show various possible constructs for the scaffold 180 including where mesh 182 thereof is joined by connectors 184 to facilitate or aid in the recoil effect as shown in FIGS. 9 and 10.

FIG. 12 shows various exemplary design shapes for the proximal surface 170 of the insert 118 these can be achieved by manipulating a shape and/or size of the plurality of bladders 164 as previously discussed. The design shapes can include standard design shapes (e.g., flat proximal surface 170 shape, a cruciate retaining ("CR") design, a medial congruent ("MC") design, an ultra-congruent ("UC") design, a posterior stabilized ("PS") design, or another standard design) or a hybrid design such as one where the lateral compartment of the insert 118 has one standard design (or non-standard personalized design) but the medial compartment of the insert 118 has a different standard design (or different non-standard personalized design). As previously discussed, the insert 118 can be shaped to shift from one shape or design for the proximal surface 170 to another by manipulation of the size and/or shape of the bladders 164. Thus, for example upon initial insertion the insert can have shape 190 but can be controlled to a second shape based upon sensor input data gathering one or more kinematics of the knee joint. This shifted second shape can be a standard shape or one personalized to the patient to achieve a maximum range of motion balanced against stability, for example.

Figure 13:
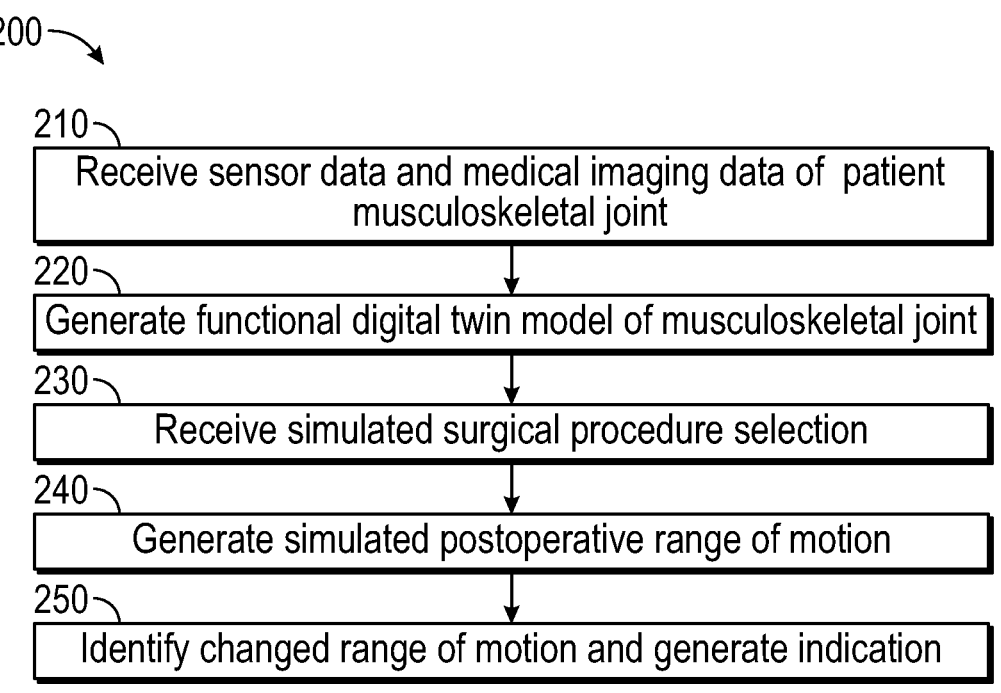
FIG. 13 illustrates a flow chart showing method of generating and applying of a functional digital twin model, in accordance with some examples of the present application.

FIG. 13 shows an exemplary method 200 of generating an arthroplasty functional digital twin that can be utilized with the insert and systems described herein. The method 200 can receive at 210 sensor data and medical imaging data of a patient musculoskeletal joint. This can include receiving first sensor data from a first plurality of sensors positioned between an insert and a first implant (e.g., the tibial prosthesis) as previously illustrated and described. The method can further include receiving second sensor data from a second plurality of sensors implanted in the patient. The first sensor data and the second sensor data characterizing one or more kinematics of a musculoskeletal joint of the patient. The method 200 can generate at 220 a functional digital twin model of the musculoskeletal joint that includes the insert, the first implant (e.g., tibial prosthesis) and/or second implant (e.g., femoral prosthesis). Generating the functional digital twin model at 220 can be based upon the first sensor data, the second sensor data and/or the medical imaging data. The functional digital twin model can simulate the one or more kinematics of the knee joint as detected by sensors (based upon the first sensor data and/or second sensor data).

From the first sensor data, the second sensor data and/or the medical imaging data such as gathered in real-time, the functional digital twin model can be updated. Alteration of the functional digital twin could be used by the surgeon to guide altering the shape and/or size of the insert. Thus, the method 200 contemplates receiving a simulated surgical selection at 230 such as, but not limited to: a selection to alter a shape and/or size of the insert, a selection to alter a shape of a proximal surface of the insert, a selection to alter slope of the insert proximal surface or the like. Such selection can result in simulating the one or more of the shape or the size of the insert with the digital twin model. The method 200 can generate a predicted one or more kinematics of the musculoskeletal joint based on the simulated surgical procedure selection with the functional digital twin model. This can include the method 200 generating at 240 a simulated postoperative range of motion of the knee join in the functional digital twin model. The method 200 can indicate or otherwise identify changed range of motion. Thus, the method can include indicating the predicted one or more kinematics of the musculoskeletal joint. This would not just be limited to range of motion but could include any one or combination of medial-lateral translation of the femoral implant and insert, anterior-posterior translation between the femoral implant and insert, joint laxity (measured by pressure or force on the plurality of sensors), femoral rotation, conformity of the proximal surface of the insert with the femoral condyles (related to joint stability), etc.

Figure 14:
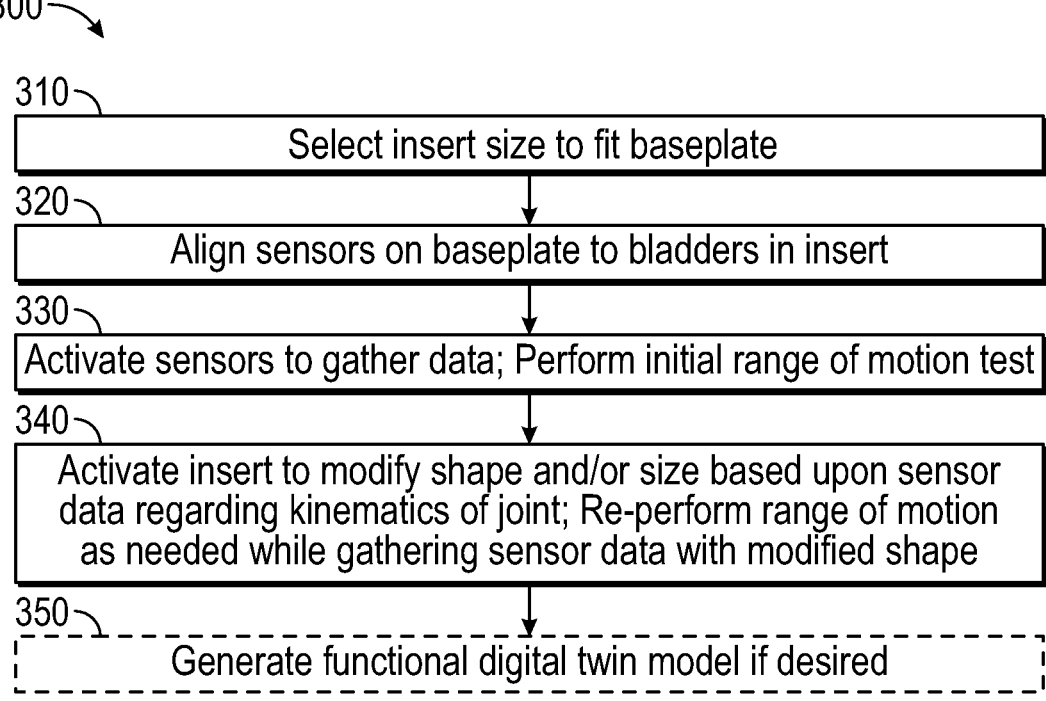
FIG. 14 illustrates a flow chart of a surgical method in accordance with some examples of the present application.

FIG. 14 shows an arthroplasty surgical method 300. Broadly, the method 300 can include various steps including selection at 310 of an insert to fit a baseplate as previously described. Prior to this step various steps can be performed by the orthopedic surgeon. These can include completing tibial and femoral cuts, removing osteophytes and perform- ing ligament releases based on subjective assessment. The surgeon can drill the tibia for the morphokinematic tibial implant (keel, battery chamber, sensor base plate, etc.) placement. Such placement can be aligned with the mechanical axis of tibia. The surgeon places femoral implant with the peg sensors and peg batteries. The sensors associ- ated with the femur or femoral implant can be activated soon after placement. The surgeon selects an insert that covers the entire circumference of the tibia, connects the insert to abut a tibial sensor surface and power point on the tibial baseplate surface. Sensors of the tibial baseplate can be aligned at 320 with and be distal to (e.g., correspond in position with) the bladders of the insert as previously discussed and shown.

Upon initial implantation of the insert, the insert can be at its highest configuration (w.r.t insert height, bladder pres- sure) and the insert can be at a maximum dimension. The insert can have medial and lateral proximal surface convex- ity. The plurality of bladders can be at high pressure so the insert will tightly fit in the joint space. The insert will come with pre-filled fluid in the reservoir and bladders. The surgeon can also manually charge the chambers with the fluids for the insert to reach the highest configuration.

All sensors can now be activated to gather data 330 and an initial range of motion for the knee joint (as much as feasible) can be performed. The insert can be activated at 340 and draws power from the tibial baseplate through the tibial battery. If implanted in one of the tibia, the femur, the insert, the tibial implant or the femoral implant, the proces- sor can be activated. The sensors (e.g., in the femoral component and on the tibial baseplate) communicate with the processor and/or each other. One femoral sensor can communicate with another femoral sensor and the femoral sensor can communicate with one or more tibial sensors. A sensor-based two-dimensional or three-dimensional map (such as illustrated in FIGS. 6A and 6B) can be created by the processor and can be relayed by the transmitter to the surgeon's tablet, phone, computer, robotic surgical device, surgical navigation equipment, etc.

Initially, upon implantation of the insert, the patient may not be able to flex the knee through a full range of motion. This can be due to the large insert size. The patient can be asked to weight bear (i.e., stand) and the insert starts regulating internal pressure within the one or more bladders by opening the valves to determine the optimum shape. Such opening and closing of the valves can be at the control of the processor and can be performed based upon sensor data, for example. The patient may gradually start flexing the knee through a full range of motion and walking. This kinematics of the joint creates a topographical map of the femoral implant contacting the proximal surface of the insert (see FIGS. 6A and 6B). The sensors capture force, pressure data, acceleration data, vector data, etc. and the controller deter- mines the exact forces (and other kinematic information) exerted on the knee joint. The insert gradually starts con- figuring itself (inflating, deflating one or more of the plu- rality of bladders) based on a most optimum shape (deter- mined by an algorithm of the processor and/or surgeon input such as informed by the functional digital twin model, etc.) to permit maximum knee flexion and extension for the given implant position and sets the constraint by changing con- gruency of the proximal surface of the insert with the femoral implant condyles. Range of motion and other kine- matic testing can be reperformed as necessary. Optionally, the method 300 can generate at 350 a functional digital twin model as previously discussed. At a follow up visit the surgeon can obtain the digital twin model and use this to assess how the implants relative positions are affecting overall implant wear and tear and the surgeon can adjust the insert shape and/or size to obtain the optimum outcome in case the surgeon feels that the insert has not reached optimum shape and size by control by the processor.

FIG. 15 illustrates an example of a block diagram of a machine 400 upon which any one or more of the techniques (e.g., methodologies) discussed herein may perform in accordance with some embodiments. In alternative embodi- ments, the machine 400 may operate as a standalone device or may be connected (e.g., networked) to other machines. In a networked deployment, the machine 400 may operate in the capacity of a server machine, a client machine, or both in server-client network environments. The machine 400 may be a personal computer (PC), a tablet PC, a personal digital assistant (PDA), a mobile telephone, a web appli- ance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud comput- ing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include con- figurable execution units (e.g., transistors, circuitry, etc.) and a computer readable medium containing instructions, where the instructions configure the execution units to carry out a specific operation when in operation. The configuring may occur under the direction of the execution units or a loading mechanism. Accordingly, the execution units are communi- catively coupled to the computer readable medium when the device is operating. For example, under operation, the execution units may be configured by a first set of instruc- tions to implement a first set of features at one point in time and reconfigured by a second set of instructions to imple- ment a second set of features.

Machine (e.g., control circuitry, processor, computer sys- tem) 400 may include a hardware processor 402 (e.g., a central processing unit (CPU), a graphics processing unit (GPU), a hardware processor core, processing circuitry, or any combination thereof), a main memory 404 and a static memory 406, some or all of which may communicate with each other via an interlink (e.g., bus) 408. The machine 400 may further include a display unit 410, an alphanumeric input device 412 (e.g., a keyboard), and a user interface (UI) navigation device 414 (e.g., a mouse). In an example, the display unit 410, alphanumeric input device 412 and UI navigation device 414 may be a touch screen display. The display unit 410 may include goggles, glasses, an augmented reality (AR) display, a virtual reality (VR) display, or another display component. For example, the display unit may be worn on a head of a user and may provide a heads-up-display to the user. The alphanumeric input device 412 may include a virtual keyboard (e.g., a keyboard displayed virtually in a VR or AR setting.

The machine 400 may additionally include a storage device (e.g., drive unit) 416, a signal generation device 418 (e.g., a speaker), a network interface device 420, and one or more sensors 421, such as those discussed herein. The machine 400 may include an output controller 428, such as a serial (e.g., universal serial bus (USB), parallel, or other wired or wireless (e.g., infrared (IR), near field communication (NFC), etc.) connection to communicate or control one or more peripheral devices.

The storage device 416 may include a machine readable medium 422 that is non-transitory on which is stored one or more sets of data structures or instructions 424 (e.g., software) embodying or utilized by any one or more of the techniques or functions described herein. The instructions 424 may also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, or associated caches and servers) configured to store the one or more instructions 424.

The term "machine readable medium" may include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 424 may further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 420 may include one or more physical jacks (e.g., Ethernet, coaxial, or phone jacks) or one or more antennas to connect to the communications network 426. In an example, the network interface device 420 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 400, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The claimed invention is:

1. An insert for replacement of a joint of a patient, the insert comprising:
   a body having a plurality of bladders therein, two or more of the plurality of bladders in fluid communication with one another, the plurality of bladders expandable and contractible in volume;
   a proximal surface shapable in situ by a change in the volume of one or more of the plurality of bladders to achieve a desired conformity along the proximal surface with a first arthroplasty implant of the patient, the proximal surface when so shaped with the desired conformity is configured to interface with and facilitate articular movement with the first arthroplasty implant of the patient; and
   a distal surface spaced from the proximal surface by the body, the distal surface configured to interface with a second arthroplasty implant of the patient.

2. The insert of claim 1, further comprising a central reservoir in selective fluid communication with the plurality of bladders, wherein the central reservoir has an inlet to receive a fluid therein from external of the insert.

3. The insert of claim 2, further comprising one or more valves positioned in the body between the central reservoir and the plurality of bladders, the one or more valves regulating a flow of a fluid between the central reservoir and the plurality of bladders.

4. The insert of claim 1, wherein the proximal surface is a hydrogel membrane.

5. The insert of claim 1, further comprising a scaffold positioned between one or more of the plurality of bladders and the proximal surface.

6. The insert of claim 1, wherein the proximal surface is shapable to achieve one of a cruciate retaining design, a medial congruent design, an ultra-congruent design, a posterior stabilized design, another standard design or a hybrid design of the cruciate retaining design, the medial congruent design, the ultra-congruent design or the posterior stabilized design.

7. A system for a knee arthroplasty, the system comprising:
   a tibial implant configured to couple to a resected surface of a tibia;
   a femoral implant configured to couple to a resected surface of a femur;

an insert positionable between the femoral implant and the tibial implant, the insert comprising:
   a body with a plurality of bladders therein, two or more of the plurality of bladders in fluid communication with one another, the plurality of bladders expandable and contractible in volume; and
   a proximal surface shaped in situ by changes in the volume of one or more of the plurality of bladders to achieve a desired conformity along the proximal surface with the femoral implant, the proximal surface when so shaped with the desired conformity is configured to interface with and facilitate articular movement with the femoral implant;
   a first plurality of sensors configured to be positioned between the tibial implant and the insert, the first plurality of sensors arranged to correspond in a position distal of the plurality of bladders;
   a second plurality of sensors coupled to one of the femoral implant or femur;
   processing circuitry; and
   a memory that includes instructions, the instructions, when executed by the processing circuitry, cause the processing circuitry to:
   receive first sensor data from the first plurality of sensors;
   receive second sensor data from the second plurality of sensors;
   determine, based upon the first sensor data and the second sensor data, one or more kinematics of a knee joint of a patient; and
   control the insert to expand or contract one or more of the plurality of bladders including to shape the proximal surface based upon the one or more kinematics.

8. The system of claim 7, wherein the memory that includes the instructions, when executed by the processing circuitry, further cause the processing circuitry to:
   receive medical imaging data of the knee joint of the patient; and
   generate a functional digital twin model of the knee joint including the insert based on the first sensor data and the second sensor data and the medical imaging data, the functional digital twin model simulating the one or more kinematics of the knee joint.

9. The system of claim 8, wherein the memory that includes the instructions, when executed by the processing circuitry, further cause the processing circuitry to:
   receive a simulated surgical procedure selection, the simulated surgical procedure selection including at least one of a size of the insert or a shape of the proximal surface of the insert;
   generate a predicted one or more kinematics of the knee joint based on the simulated surgical procedure selection with the functional digital twin model; and
   generate an indication of the predicted one or more kinematics.

10. The system of claim 8, wherein the memory that includes the instructions, when executed by the processing circuitry, further cause the processing circuitry to create a digital topography simulating a maximum range of motion with a desired constraint for a simulated proximal surface of the insert in the functional digital twin model.

11. The system of claim 8, wherein the control of the insert to expand or contract one or more of the plurality of bladders by the processing circuitry is based upon a machine learning knee joint model.

12. The system of claim 7, wherein the insert includes a centrally positioned reservoir and one or more valves positioned in the body between the reservoir and the plurality of bladders, the one or more valves are controlled by the processing circuitry to regulate a flow of a fluid between the reservoir and the plurality of bladders.

13. The system of claim 7, wherein the one or more kinematics of the knee joint include one or more of an amount of translation of the femur with respect to the tibia, an amount of rotation of the femur with respect to the tibia, and an amount of force on the first plurality of sensors.

14. The system of claim 13, wherein the one or more kinematics of the knee joint are used to create a digital topography simulating a maximum range of motion with a desired constraint for a simulated proximal surface of the insert.

15. The system of claim 7, wherein a scaffold forms a part of the body positioned between one or more of the plurality of bladders and the proximal surface.

16. The system of claim 7, wherein the insert is configured to use synovial fluid of the knee joint of the patient as a fluid for the plurality of bladders.

17. An assembly for a knee arthroplasty, the assembly comprising:

a tibial implant coupled to a resected surface of a tibia;

a femoral implant coupled to a resected surface of a femur;

an insert positioned between the femoral implant and the tibial implant and coupled to the tibial implant, the insert comprising:

a body with a plurality of bladders therein, two or more of the plurality of bladders in fluid communication with one another, the plurality of bladders expandable and contractible in volume; and a proximal surface shaped in situ by changes in the volume of one or more of the plurality of bladders to achieve a desired conformity along the proximal surface with the femoral implant, the proximal surface when so shaped with the desired conformity is configured to interface with and facilitate articular movement with the femoral implant;

a first plurality of sensors positioned between the tibial implant and the insert, the first plurality of sensors arranged to correspond in a position distal of the plurality of bladders;

a second plurality of sensors coupled to one of the femoral implant or femur;

processing circuitry mounted to one of the tibial implant or the femoral implant; and a memory that includes instructions, the instructions, when executed by the processing circuitry, cause the processing circuitry to:

receive first sensor data from the first plurality of sensors;

receive second sensor data from the second plurality of sensors;

determine, based upon the first sensor data and the second sensor data, one or more kinematics of a knee joint of a patient; and control the insert to expand or contract one or more of the plurality of bladders including to shape the proximal surface based upon the one or more kinematics.

18. The assembly of claim 17, wherein the insert includes:

a central reservoir in selective fluid communication with the plurality of bladders, wherein the central reservoir has an inlet to receive a fluid therein from external of the insert;

one or more valves positioned in the body between the central reservoir and the plurality of bladders, the one or more valves regulating a flow of a fluid between the central reservoir and the plurality of bladders; and a scaffold positioned between one or more of the plurality of bladders and the proximal surface;

wherein at least the proximal surface is formed of a material that is shapable in situ.

19. The assembly of claim 17, wherein the proximal surface of the insert is shapable to achieve one of a cruciate retaining design, a medial congruent design, an ultra-congruent design, a posterior stabilized design, another standard design or a hybrid design of the cruciate retaining design, the medial congruent design, the ultra-congruent design or the posterior stabilized design.

* * * * *